United States Patent [19]
Kibbel, Jr.

[11] 3,956,444

[45] May 11, 1976

[54] PROCESS FOR PRODUCING A RAPIDLY-SOLUBLE SODIUM DICHLOROISOCYANURATE DIHYDRATE TABLET

[75] Inventor: William Henry Kibbel, Jr., Pennington, N.J.

[73] Assignee: FMC Corporation, Philadelphia, Pa.

[22] Filed: Aug. 6, 1973

[21] Appl. No.: 385,907

[52] U.S. Cl. ................................ 264/109; 424/14; 424/249
[51] Int. Cl.² .................... A61J 3/10; B29B 1/032
[58] Field of Search ............... 264/109; 424/249, 14

[56] References Cited
UNITED STATES PATENTS

| | | | |
|---|---|---|---|
| 2,913,460 | 11/1959 | Brown et al. | 424/249 X |
| 2,921,339 | 1/1960 | Pitzer | 264/109 |
| 3,120,378 | 2/1964 | Lee et al. | 424/249 X |
| 3,175,521 | 3/1965 | Hershberg | 424/14 X |
| 3,287,359 | 11/1966 | Matzner | 424/249 X |
| 3,344,030 | 9/1967 | Stevens | 424/14 X |
| 3,412,021 | 11/1968 | Paterson | 424/249 X |
| 3,457,167 | 7/1969 | Spiegel et al. | 424/249 X |
| 3,873,685 | 3/1975 | Kibbel et al. | 424/249 X |

FOREIGN PATENTS OR APPLICATIONS

| | | | |
|---|---|---|---|
| 42-23198 | 11/1967 | Japan | 264/109 |

*Primary Examiner*—Philip Anderson

[57] ABSTRACT

Process for producing a rapidly-soluble, structurally-strong, storage-stable chlorine releasing tablet by compressing sodium dichloroisocyanurate dihydrate in a structure-forming apparatus with pressures from about 2,000 to about 10,000 p.s.i.

2 Claims, No Drawings

PROCESS FOR PRODUCING A RAPIDLY-SOLUBLE SODIUM DICHLOROISOCYANURATE DIHYDRATE TABLET

This invention relates to a process of producing a rapidly-soluble, structurally-strong, storage-stable tablet that resists deterioration and dimensional change due to moisture, and supplies active chlorine when placed in an aqueous solvent, by compressing sodium dichloroisocyanurate dihydrate in a mold, die, or press at a pressure of about 2,000 to about 10,000 p.s.i.

Chlorine-releasing agents that give off available chlorine when placed in water have been used as bactericides to kill bacteria and to prevent their growth in swimming pools, portable water supplies and the like. Chlorination has been accomplished by a variety of means using gaseous chlorine, solutions of chlorine-releasing agents, or solid forms of agents which release chlorine. The safest and most popular chlorine-releasing agents used are the solid compositions, which may be in either granular or tabletted form. Tablets are preferred over granular materials because they obviate the need for measuring cups and eliminate the problem of spillage and storage of bulky materials.

The tabletted chlorine-releasing compositions so far produced, have been either rapid-dissolving or slow-dissolving. Rapid-dissolving tablets are effective in supplying available chlorine quickly to pool water, for example, in response to changing chlorine demands put upon the pool water. Slow-dissolving tablets, on the other hand, are effective in maintaining available chlorine in pool water at a given rate over long periods of time. Tabletted anhydrous sodium dichloroisocyanurate is an example of a chlorine-releasing composition that is rapid-dissolving. Anhydrous sodium dichloroisocyanurate tablets which have physical properties suitable for packaging and shipping are formed only with difficulty under high pressures (around 60,000 p.s.i.). Use of these high pressures results in some decomposition of the anhydrous material causing a decrease of available chlorine in the final product. Once formed, the tablets are not dimensionally stable; that is, they swell and develop structurally weak efflorescent structures upon prolonged exposure to high humidities or small amounts of moisture. Furthermore, compositions containing anhydrous sodium dichloroisocyanurate have been successfully tabletted only when a lubricant such as boric acid (see U.S. Pat. No. 3,120,378) or stabilizers such as boron oxide and sodium carbonate (see French Patent No. 1,537,311) have been employed during the molding process. Such additives are objectionable in-so-far as they act as diluents and thereby decrease the available chlorine content of the compositions. The additives also act as impurities which are often undesirable. These processes do not overcome the basic drrawback of tabletting anhydrous sodium dichloroisocyanurate, namely, that it does not tablet easily at conventional pressures of about 15,000 to 25,000 p.s.i. Consequently, the above processes are not commercially feasible, since the pressures needed to tablet the anhydrous material to produce a satisfactory tablet put excessive strain on the tabletting machinery causing extensive wear of the tabletting machinery, and result in decomposition of the chlorine-releasing agent.

Takuo Shinshige (Japanese Patent Publication No. 1967-23198) discovered that the addition of water within a specific range enabled various types of chlorocyanurate powders to be molded without the above problems, and allowed the subsequent granulation of the tablets to form granular materials with increased specific gravities. In one example, Shinshige was able to continuously tablet sodium dichlorocyanurate when the compound contained 4 to 14% moisture under a conventional compression pressure of 1,000 kilograms/square centimeter (approximately 15,000 pounds/square inch). This compression pressure, however, produces a tablet with a relatively long dissolution time of around 15 minutes. Such dissolution times are not sufficiently to immediately combat bacterial growth such as is encountered in the entire area of a swimming pool. Dissolving times of 5 minutes or less are required for such immediate bacterial action. Consequently, the patentee granulates this material and forms a faster dissolving, higher specific gravity material. Granular material, however, when used as a chlorine-releasing agent lacks the simplicity and convenience afforded by a tabletted product.

Tabletted trichloroisocyanuric acid and tabletted calcium hypochlorite are examples of slow-dissolving chlorine-releasing tablets. These tablets have dissolution times ranging from hours to days, which permits the release of available chlorine at one specific rate over long periods of time. This slow solubility rate, however, has insufficient flexibility to permit the tablets to be effective as a bactericide in responding to rapid changes in chlorine demands put on pool water occassioned by variations in climate or swimmer load.

It is the object of the present invention to produce a rapidly-soluble, structurally-strong, storage-stable tablet which is easily formed and which is resistant to deterioration or dimensional change due to moisture.

I have made the surprising discovery that a rapidly-soluble, structurally-strong, storage-stable tablet that resists structural changes due to moisture can be formed without loss of available chlorine by compressing sodium dichloroisocyanurate dihydrate in a structure-forming apparatus, such as a press, mold or die, at a pressure of about 2,000 to about 10,000 psi. The sodium dichloroisocyanurate dihydrate tablets form easily without lubricants or stabilizers, and maintains its dimensional stability for extended periods of time. The tablets are easily dispersed and provide for the rapid release of chlorine to meet varying sanitizing needs; these advantages previously have not been available with other chlorine sources.

The term "sodium dichloroisocyanurate dihydrate" means a hydrated sodium dichloroisocyanurate containing 14.1% by weight water of hydration. Hydrated sodium dichloroisocyanurate containing less than 14.1% by weight water of hydration may be mixed with the dihydrate in minor concentrations and used in the process of the invention.

Tablets of sodium dichloroisocyanurate dihydrate are prepared by placing particulate, i.e. either granular or crystalline sodium dichloroisocyanurate dihydrate into a structure-forming apparatus such as a press, mold, or die and pressing them to form the chlorine-releasing tablets. The pressure used to press these tablets will vary depending upon the rate at which the tablet is to dissolve. This rate is termed the "solubility rate" and is the time it takes a tablet (1 inch diameter by ⅜ inch thick) to dissolve and escape from a ½ inch stainless steel mesh cage immersed in 1 liter of swirling distilled water at 20°C. Rapidly-soluble tablets have solubility rates of about 5 minutes and preferably between 0.5 and 3 minutes. In general, the pressures necessary to obtain this rapid solubility rate range from about 2,000 to about 10,000 p.s.i. Pressures between 2,000 and 5,000 p.s.i. produce tablets with a solubility rate of around 30 seconds. Pressures above 5,000 but below 10,000 p.s.i. produce tablets with solubility rates of a few minutes. Pressures below about 2,000 p.s.i. do not produce an acceptable tablet. These tablets are generally difficult to remove from the die, they have weak corners and have poor structural strength and hardness. Pressures above about 10,000 p.s.i. should be avoided since these pressures produce tablets with slow solubility rates, that is above about 5 minutes. Such slow solubility rates are not effective to immediately combat bacterial growth, for example, in the entire area of a swimming pool.

The tablet may contain conventional additives such as coloring matter, various dyes, perfumes and the like. These tablets do not require fillers as do detergent tablets, even though the tablets of this invention may contain fillers to increase the size of the tablet for ease of handling and dispensing. The desired additives are simply blended with the sodium dichloroisocyanurate dihydrate and the blended formulation is tabletted.

In the tabletting procedure of this invention, it has been found that the pressed material does not adhere to the dies, and there is no capping during the pressing of the material. The term "capping" refers to the internal horizontal separation of the tablet into two or more pieces because of the adherence of these pieces to each of the dies. The tablets may be easily removed from the die. The overall appearance is excellent, with the tablets having strong corners and excellent hardness. In general, the use of standard dies is eminently satisfactory without special provision for rotation of the dies during the pressing operation.

The tablet of this invention, may be used as a source of available chlorine in treating swimming pools or in other applications which require chlorine treatment of water.

When the sanitizer tablet of this invention is used in swimming pools, it is preferred to place the tablet in the pool skimmer. The skimmer is normally used as the water intake of a recirculating system for constant purification and circulation of pool water. The resulting intake water constantly flows over the tablet, rapidly releasing available chlorine into the intake water stream.

The number of tablets added to a pool is that number which will replace the active chlorine dissipated during normal pool use. When climatic conditions or heavy swimmer load result in excessive chlorine dissipation, additional tablets are merely added. The immediate addition and dissolution of the tablets to yield available chlorine is necessary to prevent the growth of bacteria which are present in the water. Excess concentrations of available chlorine in the pool that may irritate the eyes and mucous membranes of the swimmers are not produced. The tablets do not leave any unsightly, white residue on pool surfaces, as is the case with slower-dissolving chlorine-releasing agents. Since the tablets leave no residue, they are truly maintenance free.

Where a recirculating system is not used or the tablets cannot be conveniently used in this manner, or when water other than in swimming pools is to be treated, the tablets may be added directly to the water.

When sanitizing bodies of water other than in swimming pools, the number of tablets added to the aqueous solution is that number which will kill the bacteria which are present. When treating an aqueous solution for the first time it is generally necessary to employ an excess of tablets to superchlorinate the solution. This results in rapid and complete destruction of bacteria prevents bacterial growth. After this initial dosage, tablets may be added to the solution in an amount which merely replaces the active chlorine dissipated so as to maintain the solution virtually bacteria free.

The term "tablet" as used herein refers not only to that product which is obtained by compressing sodium dichloroisocyanurate dihydrate in a mold press or die to form a unitary pressed shape of any geometric configuration, but also refers to any product which is compressed into a dense shape, whether or not this dense shape is subsequently left intact or whether it is subdivided into individual discrete pieces of smaller size.

The following examples are given to illustrate the present invention but are not deemed to be limiting thereof.

EXAMPLE 1-A

Process of the Invention

Tablets of sodium dichloroisocyanurate dihydrate were prepared by placing 15 grams of granular sodium dichloroisocyanurate dihydrate into a Carver Laboratory Hand Press having a stainless steel die cavity. A tabletting force was applied through a mating stainless steel plunger. The tabletting force or pressure applied is set forth in Table I. Tablets (1 inch diameter by ⅜ inch thick) were tested for hardness in a Strong, Cobb, Arner Hand Tester. One tablet was placed in the Hand Tester and the force necessary to crush the tablet was measured. Hardness was not tested above 25 kilograms/square centimeter since this is the normal strength required for packaging and handling. The solubility rate was measured by supporting one tablet (1 inch diameter by ⅜ inch thick) in a ½ inch stainless steel mesh cage which was suspended in 1 liter of swirling distilled water at 20°C. The time required for the tablets to completely dissolve and escape from the mesh cage was measured. Results are set forth in Table I.

Table I

| Pressure (PSI) | Tablet Appearance | Hardness (Kg) | Solubility (min.) |
|---|---|---|---|
| 5,000 | Easy removal from die porous strong | >25 | 0.5 |
| 10,000 | Easy removal from die porous strong | >25 | 3 |

This example shows that the sodium dichloroisocyanurate dihydrate tablets produced with pressures of 5,000 and 10,000 p.s.i. displayed good physical properties. They had strong corners, good hardness, easy removal from the die and were rapidly-soluble.

EXAMPLE 1-B

Comparative Process

The process of Example 1 was repeated except that granular anhydrous sodium dichloroisocyanurate and trichloroisocyanuric acid were used in place of sodium dichloroisocyanurate dihydrate. The results are set forth in Tables II and III.

Table II

| Pressure (PSI) | Anhydrous Sodium Dichloroisocyanurate Tablet Appearance | Hardness (Kg) | Solubility (min.) |
| --- | --- | --- | --- |
| 5,000 | Squeaky and difficult removal from die porous weak corners | 13.5 | 1.5 |
| 10,000 | Squeaky and difficult removal from die less porous weak corners | 22 | 3 |

Table III

| Pressure (PSI) | Trichloroisocyanuric Acid Tablet Appearance | Hardness (Kg) | Solubility (hours) |
| --- | --- | --- | --- |
| 5,000 | Easy removal from die porous weak corners | 24 | 16 |
| 10,000 | Easy removal from die slightly porous weak corners | >25 | 20 |

The data in Table II shows that tabletted anhydrous sodium dichloroisocyanurate was rapidly soluble and difficult to remove from the die. The tablets showed poor hardness and weak corners.

The data in Table III shows that tabletted trichloroisocyanuric acid was very slowly soluble and easy to remove from the die. The tablets had a reasonable hardness but the corners were weak.

EXAMPLE 2

This example compares the resistance of anhydrous sodium dichloroisocyanurate and sodium dichloroisocyanurate dihydrate tablets to deterioration and dimensional change upon wetting or prolonged exposure to high humidities.

A fine water mist was sprayed for two hours onto sodium dichloroisocyanurate dihydrate and anhydrous sodium dichloroisocyanurate tablets produced according to Example 1-A and Example 1-B. The sodium dichloroisocyanurate dihydrate tablets of this invention remained substantially unchanged. The anhydrous sodium dichloroisocyanurate tablets increased significantly in volume and developed a weak, efflorescent structure.

The invention being thus described, it will be obvious that the same may be varied in many ways. Such variations are not to be regarded as a departure from the spirit and scope of the invention, and all such modifications are intended to be included within the scope of the following claims.

What is claimed is:

1. A process for producing a rapidly-soluble, structurally-strong, storage-stable tablet of sodium dichloroisocyanurate dihydrate which comprises placing a particulate material consisting essentially of sodium dichloroisocyanurate dihydrate into a structure forming apparatus, compressing the sodium dichloroisocyanurate dihydrate with a compression pressure of about 2,000 to about 10,000 p.s.i., and recovering a rapidly-soluble, structurally-strong, storage-stable tablet which is resistant to deterioration and dimensional change due to moisture.

2. The process of claim 1 wherein a pressure of 5,000 p.s.i. is used to compress the sodium dichloroisocyanurate.

* * * * *